United States Patent [19]

Tikka et al.

[11] Patent Number: 4,718,979
[45] Date of Patent: Jan. 12, 1988

[54] METHOD FOR RAPID DETERMINATION OF THE CONTENTS OF LIGNIN, MONOSACCHARIDES AND ORGANIC ACIDS IN THE PROCESS SOLUTIONS OF SULFITE PULPING

[75] Inventors: Panu Tikka, Espoo; Nils-Erik Virkola, Helsinki, both of Finland

[73] Assignee: Oy Advanced Forest Automation Ab, Finland

[21] Appl. No.: 819,136

[22] Filed: Jan. 15, 1986

Related U.S. Application Data

[63] Continuation-in-part of Ser. No. 543,120, Oct. 18, 1983, abandoned.

[51] Int. Cl.⁴ .......................... D21C 3/04; D21C 3/22
[52] U.S. Cl. ........................ 162/49; 162/61; 162/83; 436/175
[58] Field of Search ............... 162/49, 238, 50, 198, 162/262, 83, 61, 62; 436/175, 161, 164, 129, 94; 210/662

[56] References Cited

U.S. PATENT DOCUMENTS 4,086,129  4/1978  Conca et al. .......................... 162/49

FOREIGN PATENT DOCUMENTS 69132  1/1986  Finland .
53-111103  9/1978  Japan ..................... 162/49

OTHER PUBLICATIONS

Flashka et al, "Quantitative Analytical Chemistry, 2nd Ed."; Willard Grant Press; Boston, pp. 521-523; 1980.
Felicetta et al, "Spent Sulphite Liquor VII"; *TAPPI*, vol. 42, No. 6, Jun. 1959 pp. 496-502.
Shaw, "Determination of Sugars in Waste Sulphite Liquor", *Can. Pulp & Paper*, 10 (1957); 11, 49-50.
Patterson et al, "The Spectrophotometric Determination of Lignin in Sulphite Cooling" Pulp & Paper Canada, 11-1951, pp. 105-111.

*Primary Examiner*—Steve Alvo
*Attorney, Agent, or Firm*—Scully, Scott, Murphy & Presser

[57] ABSTRACT

A method for rapid determination of the contents of lignin, monosaccharides and organic acids in the process solutions of sulfite pulping. Accordingly, any non-ionized compounds that disturbs the measurement of these concentrations are separated from the lignin material by an ion-exclusion technique. The measurements of concentrations are carried out by means of the UV-method, refractive-index method, and/or by means of the polarimetric method. The method of the present invention is usable for the controlling of sulfite cooking or other pulping or by-product production processes as well as for the characterization of the spent liquor.

4 Claims, 7 Drawing Figures

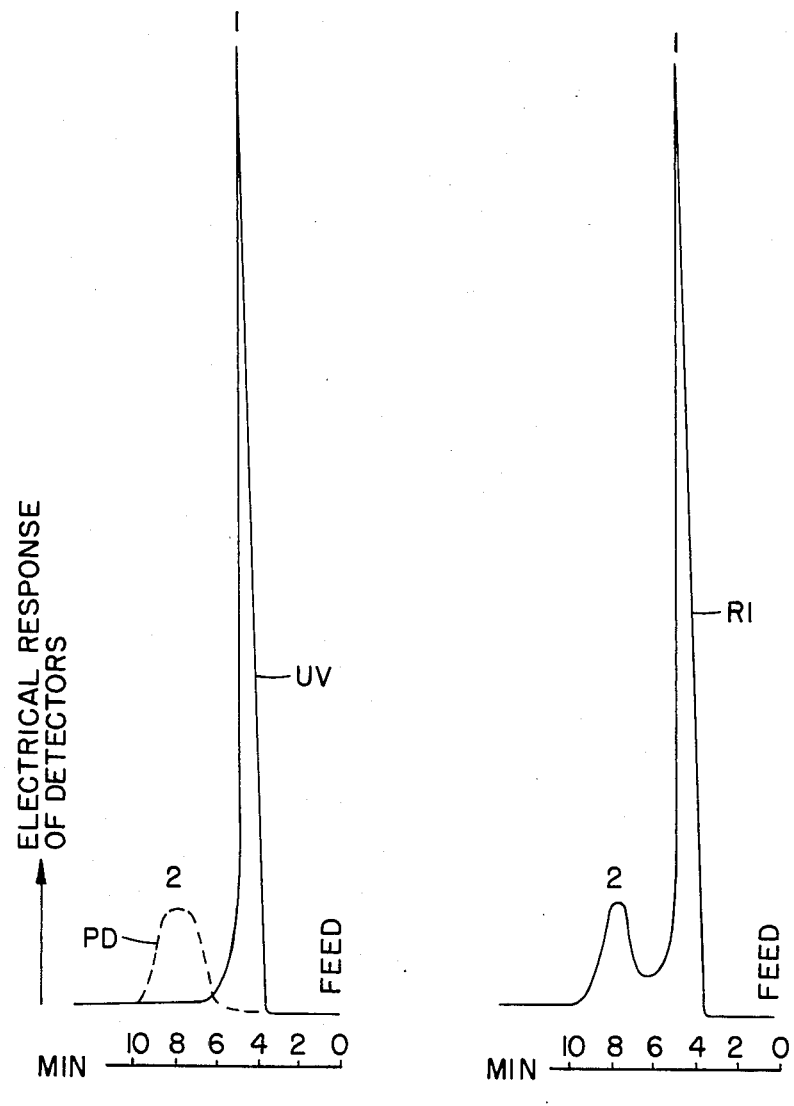
FIG. 1 SEPARATION BASED ON ION EXCLUSION, ACID COOKING LIQUOR OF ACID SULFITE COOK FROM THE END OF COOK

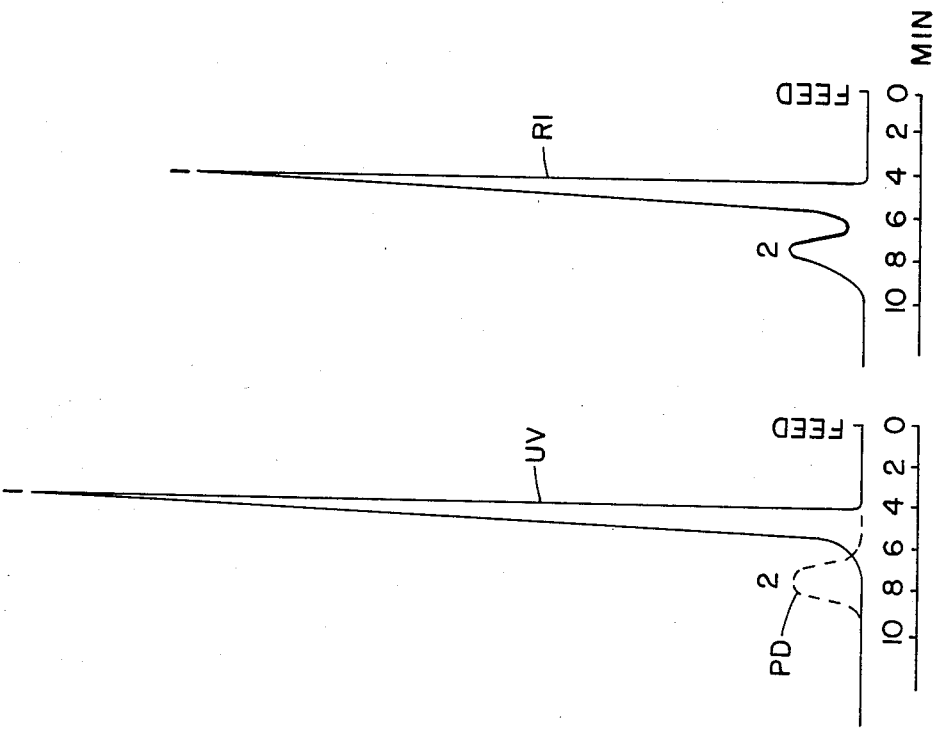
FIG. 3 ACID MAGNESIUM SULFITE COOKING END OF COOK
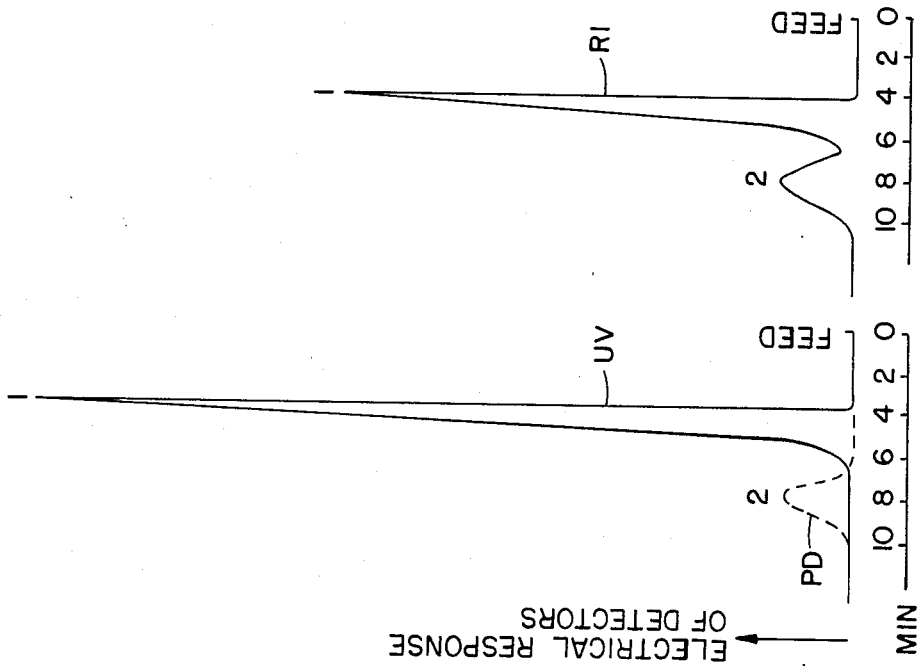
FIG. 2 ACID CALCIUM SULFITE COOKING END OF COOK

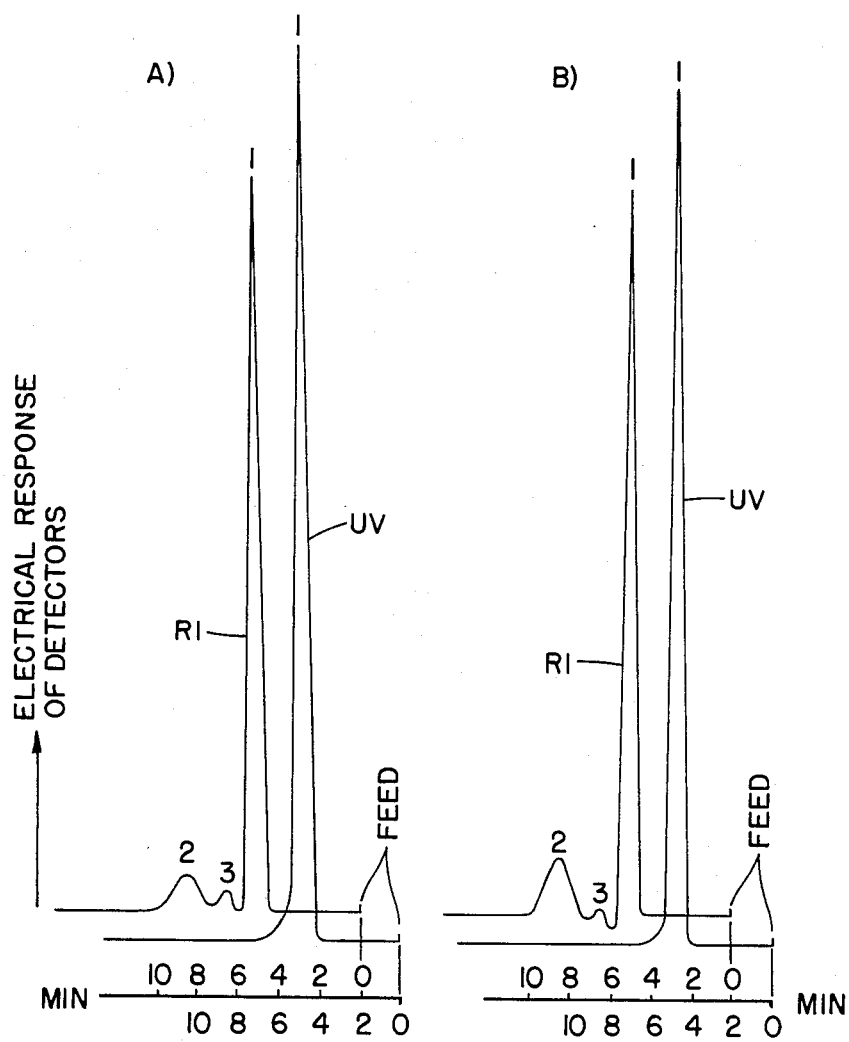
FIG.4 MULTI-PHASE SODIUM SULFITE COOKING
A) END OF SODA PHASE
B) END OF ACID PHASE FIG.5 SODIUM-NEUTRAL-SULFITE-ANTHRAQUINONE COOKING, END OF COOK
FIG.6. VERY RAPID SEPARATION AND MEASUREMENT, ACID SULFITE COOKING, END OF COOK
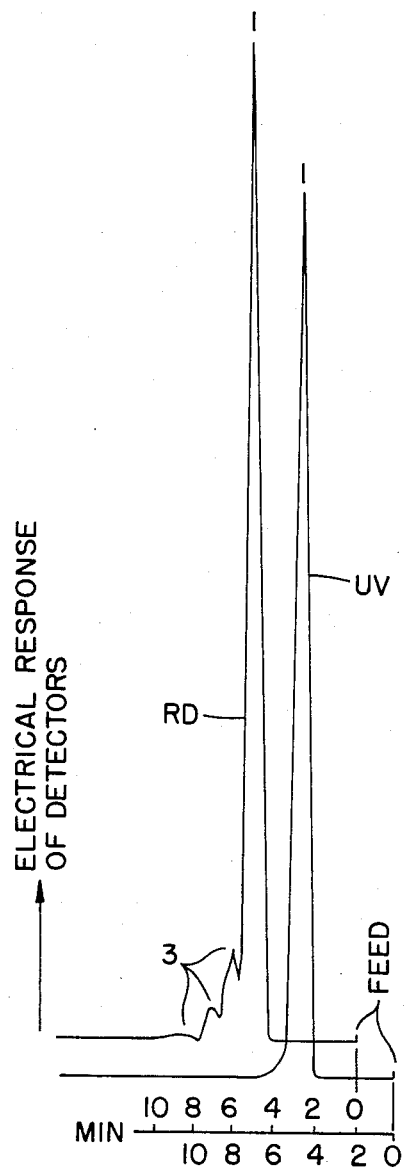
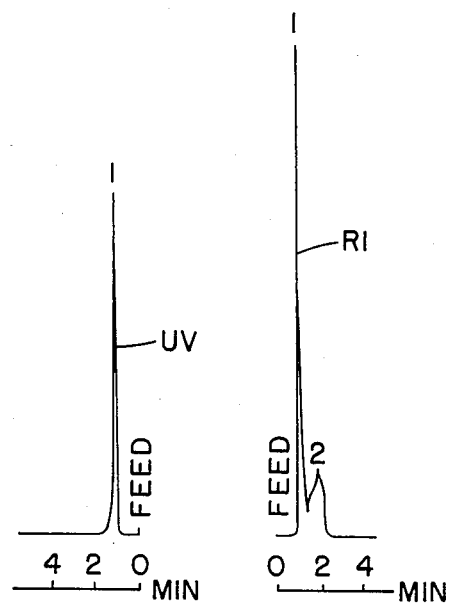

METHOD FOR RAPID DETERMINATION OF THE CONTENTS OF LIGNIN, MONOSACCHARIDES AND ORGANIC ACIDS IN THE PROCESS SOLUTIONS OF SULFITE PULPING

CROSS REFERENCE TO RELATED APPLICATIONS

This application is a continuation-in-part of application Ser. No. 543,120, filed Oct. 18, 1983, now abandoned.

BACKGROUND OF THE INVENTION

The present invention relates to a method for the rapid determination of the contents of lignin, monosaccharides and organic acids in the process solutions of sulfite pulping.

The objective of the invention is to provide a method for obtaining measurement information on the contents of sulfonated dissolved lignin, monosaccharides and organic acids at short time intervals for the purpose of controlling sulfite cooking or other pulping or by-product production processes and for the characterization of the spent liquor.

The present invention is characterized in that any non-ionized compounds that can disturb the UV-absorption and other measurements are separated from the lignin material. The separation is accomplished by an ion-exclusion technique and that the measurements of contents are performed out of the liquid flow coming out from the separation column by means of the UV-method at a wavelength of 280 nm or 260 nm, by means of the refractive-index method, and/or by means of the polarimetric method.

In the paper by Shaw A. C., "Determination of Sugars in Waste Sulphite Liquor," *Can. Pulp Paper Ind.* 10(1957):11, 49–50, it is suggested that the ion-exclusion phenomenon should be used for the purification of the sugars of sulfite spent liquor before the determination of reducing sugars. Later, in other studies, the ion-exclusion technique has been used for lignosulfonate-sugar separations in laboratory studies (see, e.g., Felicetta C. F., Lung M., McMarthy J. L., "Spent Sulphite Liquor VII. Sugar-lignin Sulphonate Separations Using Ion Exchange Resins." *TAPPI* 42(1959):6, 496–502). The method has been slow, the separations have taken from an hour to several hours, and the purpose has been to perform a group separation for further analyses in view of properties and identification of the compounds in sulfite spent liquor. Ion exclusion has not been suggested in the prior art for direct determinations of contents, but it has rather been a step of preliminary treatment before different methods of determinations of contents, are performed in the laboratory manually. The most important feature of the present invention, is the elimination of compounds disturbing the UV-measurement of lignin by means of ion exclusion.

In prior art, attempts have been made to obtain the information on contents provided by the present method by direct measurements out of the process solutions. However, these measurements have been less than successful.

Traditionally, the progress of sulfite cooks has been observed visually by comparing the colour of the cooking liquor with a color standard. In the 1950's and 60's, colorimeters were introduced in the measurement of the color. This technique allowed the observation of the transparency of the solution at a certain wavelength of visible light (Meindl N., *Lichtabsorptionsmessungen an Kochsauren, im Zusammenhanq mit dem Augschlussgrad und der technologischen Anwendung in der Sulfitzellstoff-herstellung*. Doctor's thesis, Technische Hochschule Grantz, 1961). On the basis of colorimetric measurement of the color of the cooking liquor, automation of sulfite cooking became possible. (AT Patent No. 212,687).

In the 1950's, lignin measurement based on the absorption of UV-radiation was also suggested as a basis for the cook control. In principle, UV-spectrophotometric determination of lignin can be performed at the extreme values of the UV-spectrum. Such values range from 200 to 205 nm and 280 nm to 260 nm. The "shoulder" measurement at 230 nm was also suggested. In a paper by Patterson R. F., Keays J. L., Hart J. S., Strapp R. K., Luner P., "The Spectrophotometric Determination of Lignin in Sulphite Cooking Liquor." *Pulp paper mag. Can.* 52(1951), 105–111, lignin measurement at 280 nm was suggested. It was, however, noticed that, during cooking, UV-absorbing compounds not derived from lignin were produced which caused error in the measurement, particularly in the final stage of the cooking. In the paper by Kleinert T. N., Joyce C. S., "Short Wavelength Ultraviolet Absorption of Lignin Substances and its Practical Application in Wood Pulping." *TAPPI* 40(1957):10, 813–821, measurement at 205 nm was suggested by means of very thin cuvette together with a diluting device. Later, it has been established (Schoning A. G., Johansson G., "The Ultraviolet Absorption of Sulfite Waste Cooking Liquor." *Svensk papperstidn.* 62(1959), 646–658, and Sjostrom E., Haglund P., "Spectrophotometric Determination of the Dissolution of Lignin During Sulfite Cooking." *TAPPI* 47(1964):5, 286–291 that sulfur dioxide interferes with the measurement at 205, and the measurement, consequently, does not represent lignin alone.

It is, therefore, one object of the present invention to provide a novel method to control the process solutions of sulfite pulping.

It is another object of this invention to provide a method of obtaining measurement information on the contents of sulfonated dissolved lignin, monosaccharides and organic acids at short time intervals for controlling sulfite cooking or other pulping or by product production processes.

Another object of this invention is a method for obtaining measurement information on the contents of the spent liquor.

The achievement of these and other objects will be apparent from the following description of the subject invention.

BRIEF DESCRIPTION OF THE DRAWINGS

FIG. 1 illustrates the separation of the acid cooking liquor of the acid sulfite cook from the end of cook by ion exclusion.

FIG. 2 illustrates the separation of the acid calcium sulfite cooking from the end of cook by ion exclusion.

FIG. 3 illustrates the separation of acid magnesium sulfite cooking from the end of cook by ion exclusion.

FIG. 4 illustrates the separation of a multi-step sodium sulfite cook, (A) end of soda step, (B) end of acid step by ion exclusion.

FIG. 5 illustrates the separation of sodium-neutral-sulfite-anthaquinone cooking from the end of cook by ion exclusion.

FIG. 6 illustrates the separation and measurement of acid sulfite cooking liquor from the end of cook by ion exclusion.

SUMMARY OF THE INVENTION

Figure 7:
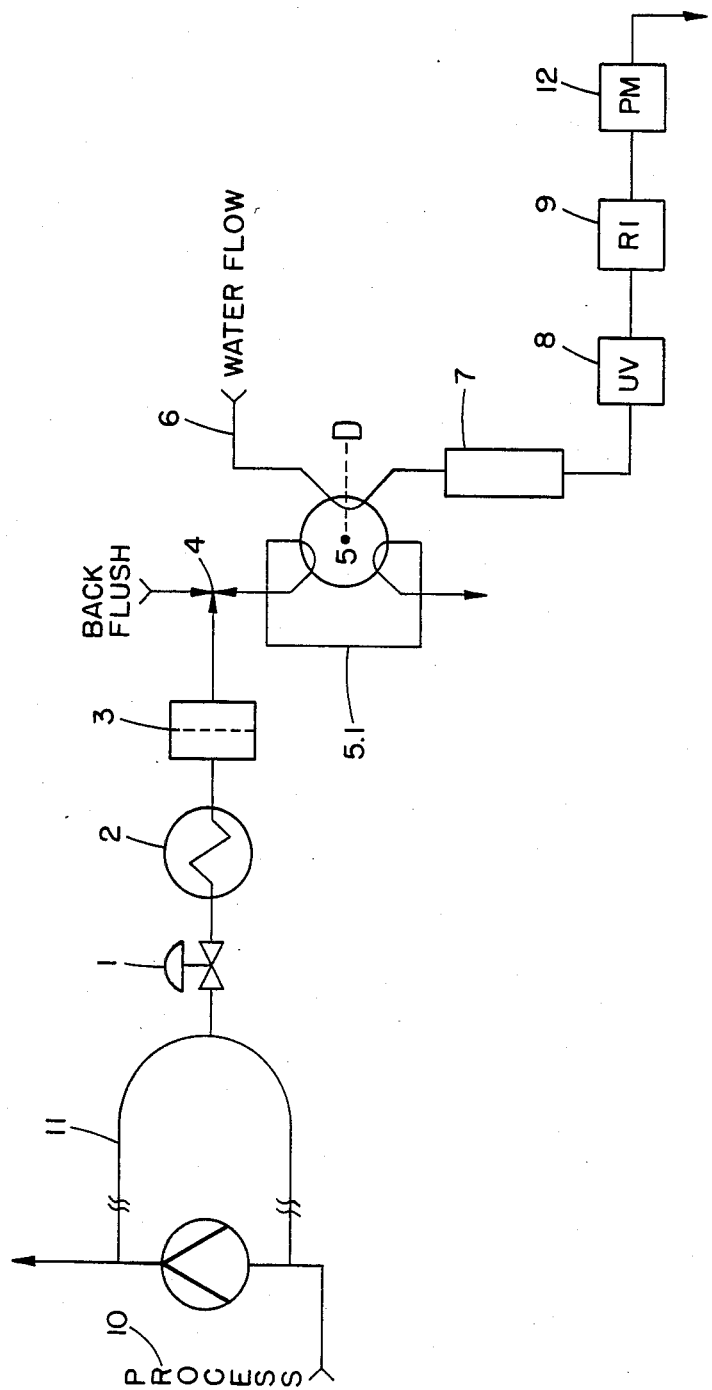
FIG. 7 illustrates the analyzer arrangement of the present invention.

These and other objects are achieved by controlling a sulfite cooking process by determining the lignin, monosaccharide and organic acid contents of the sulfite cooking liquor.

In particular, this invention relates to a method for controlling a sulfite cooking process by determining the lignin, monosaccharide and organic acid contents of sulfite cooking liquor comprising:

(a) passing a quantity of sulfite cooking liquor containing lignin and monosaccharides, lignin and organic acid, or lignin, monosaccharides and organic acids from a sulfite cooking process through a body of cation exchange material under ion-exclusion separation conditions effective to provide an effluent containing a substantially ionic portion and a substantially non-ionic portion;

(b) analyzing said effluent by determining the content of lignin by U.V. light and by refractive index, of non-lignin, i.e. monosaccharides, by polarimetry and of organic acids by refractive index; and (c) terminating the sulfite cooking process when the lignin, monosaccharide and organic acid contents reach desired values.

DETAILED DESCRIPTION OF THE INVENTION

The novel method of the present invention provides a more precise control mechanism for process solutions of sulfite pulping or other by-product production processes. Further, this invention provides a method for obtaining measurement information of the contents of the spent liquor.

In accordance with this invention, lignin measurement can be performed undisturbed by any other compounds. The lignin measurement is facilitated by a separation technique that allows the sample to be diluted for measurement with conventional apparatuses with flow-through cuvettes. Direct measurement out of the spent liquor always requires a more complex dilution procedure.

Another advantage of the method of the present invention is that it is possible to determine the contents of monosaccharides and even of organic acids. Such a measurement has not been suggested in prior art as a source of information for the controlling of processes.

Moreover, this novel method offers an opportunity for the recovery of pure fractions for further analyses, either on-line or manually.

Accordingly, the measurement of lignin is carried out as based on absorption of ultraviolet radiation or on changes in the refractive index.

The determination of the lignin concentration in the process liquor sample can be accomplished by the following procedure. The lignin fraction, which contains all the dissolved lignin from the wood but no other components, flows through the ultraviolet detector 8 and differential refractive index detector 9.

Inside the UV-detector the column effluent flows through a quartz flow-cell and UV 280 nm radiation is passed through the cell. The UV absorbing chemical parts of the lignin molecule decrease the intensity of the radiation and absorbance is measured. The sample volume, flow rate and dilution by diffusion in the column liquids meets the linear range of the detector and the Lambert-Beer law is valid for the concentration calculation where:

$$A = abc$$

Where
A is the measured absorbance
a is the absorptivity of lignin, 13 l/g cm
b is the optical radiation path of the flow-cell, 0.4 mm
c is the concentration All the absorbance of the original sample is measured by means of an integrating calculation, which generates the sum of the sample absorbance shown through the cell with respect to the time. The absorbance sum is the integration of the relative concentration of lignin in the sample and can be converted to an absolute concentration by analyzing known measured laboratory samples and calibrating the readings.

The lignin fraction also flows through the differential refractive index detector. The working principle is believed to be based on the fact that all components dissolved in water increase their refractive index. In the detector, a double flow-cell, with one side for the flow of column effluent and the other for the flow 6, is utilized. Thus only the refractive index difference caused by the sample is measured. The total amount of refractive index and thus the dissolved material is determined in the same way as determined in the UV-measurement.

The measurement of carbohydrates is carried by polarimetry, i.e. the extent of rotation of polarized light, or on changes in the refractive index. The determination of monosaccharides and organic acids in the process liquid sample can be accomplished by the following procedure. These components form a group of dozens of compounds, and they are separated from the sample as the non-lignin fraction which is eluted in 4 minutes from the column. The total amount of material in the sample is determined by integrating the material in the sample is determined by integrating the sum of refractive index difference while the non-lignin fraction flows through the detector.

The concentration of pure organic acids can be determined by calibrating the refractive index detector and polarimeter detector with a known monosaccharide solution and substracting the reading of polarimeter converted to refractive index difference from the non-lignin total refractive index difference. It is an essential feature of the present invention that any non-ionized compounds that interefere with the measurements of lignin by means of UV or by other means are separated before the measurement. At the same time, the monosaccharides are separated, which can be determined without interference by the intensive color of lignin.

The specific determination of monosaccharides is believed to be possible bacause of the asymmetric (chiral) carbon atoms found in the monosaccharide molecules. These carbon atoms and its substitutes have the ability to rotate the oscillation plane of polarized light passed through the solution containing dissolved monosaccharides. The amount of the rotation caused by the monosaccharides can be measured by means of a compensation polarimeter and thus the monosaccharide determination is achieved. This reading is a precise monosaccharide measurement because there are no other polarized light plane rotation causing components in the sulfite cooking liquids. The sum of optical polarization rotation is calculated by integrating the measured difference in rotation when the non-lignin fraction passes through the polarimeter flow-cell.

The injection-separation-detector-integrationconcentration determination method used in the present invention is used widely in analytical chemistry, especially in gas and liquid chromatographic methods.

The present invention utilizes this well known technique for cooking analysis and to produce versatile and real-time data for process control's needs. These analytical methods, e.g. chromatography, do not offer useful determinations for liquids containing dissolved wood because these methods have been developed for high resolution analysis of well dissolved dozens or hundreds of components and the cooking liquid's number of components far exceeds the capability of known methods. However, the high resolution chromatography requires special instruments and time which make it unsuitable for rapid control analysis in the mill environment. Accordingly, the present method monitors suitable groups of components, which describe the important reactions in the digester. This idea led to the development of a simple but effective purification of the lignin by the ion exclusion column separation which enables the determination of the non-lignin fraction. Thus, the present invention offers the first true and rapid lignin determination and non-lignin (carbohydrate losses) determination in less than 5 min. which allows effective cooking and pulp quality control.

The readings measured for lignin, monosaccharides and organic acids can be used easily to describe the end properties of the pulp reacting in the digester. Relative lignin concentration obtained from UV and refractive index detector is fed into a multivariable regression analysis equation in combination of initial wood and cooking acid data. This is correlated to the residual lignin concentration, the kappa-number. By this technique, several mathematical models for individual mill digesters and the kappa-number estimates obtained from this models have proven more accurate than any known cooking control kappa-number estimates.

The same procedure can be used for non-lignin results obtained from refractive index detector. End property models can be generated for yield loss and alpha-cellulose percentages (the more non-lignin material is dissolved the lower the yield and the higher the alpha-cellulose content).

The monosaccharide concentration obtained from polarimeter detector can be used directly to estimate the amount of fermentable material in cooking liquid and spent liquor for alcohol or protein production.

The chromatography-like technique for separation of the components of the liquor is well known in the art and is described in every analytical chemistry textbook. Separation takes place by ion-exclusion-chromatography based on the separation of ionizable and non-ionizable compounds from each other on the basis of their ionic nature. The separation is induced by means of a simple column filled with a cation-exchange material. When the cation-exchange material is in the cation form of the sample, the ionizable compounds in the sample cannot be diffused on the resin particles owing to electrical repulsion forces and to the retaining of electroneutrality. For the non-ionizable compounds, there is no such restriction, and under suitable conditions, they may be diffused on the resin, whereas their passage is retarded as compared with the ionizable compounds when the column is eluted with water. In the case of sulfite process solutions, the sulfonated ionizable lignosulfonates are separated from monosaccharides, furfural, weak acids, etc. non-ionizable compounds. A typical sulfite spent-liquor separation is seen in the attached FIG. 1. In this figure and in other figures, numeral 1 refers to ionizable compound, lignosulfonate, 2 refers to non-ionizable compounds, mainly monosaccharides and other compounds interfering with the lignin measurement, and 3 refers to organic acids. The designation UV means $UV_{280}$-absorption as measured by means of an ultraviolet detector, PD means the extent of optical rotation as measured by means of a polarimeter detector, RI means the change in the refractive index as measured by means of a refractometer or RI detector, and RD means the change in the refractive index as measured by means of a polarimetric detector. A more in depth discussion of chromatography is found in the *Encyclopedia of Chemistry* (S. Parker ed. 1983) 182–189, the entire contents of which are herein incorporated by reference.

When the UV-absorption, refractive index, and extent of rotation of polarized light of the outcoming liquid flow are measured after being separated by an exclusion, the contents of lignin and monosaccharides can be determined by the areas or heights of the concentration peaks. By means of integrators connected to the measurement detectors, the concentration data are obtained directly in electrical form.

Unlike the other constituents of wood, lignin absorbs ultraviolet radiation strongly, which results from the aromatic nature of lignin. The determinations based on the UV-absorption of lignin are usually carried out at the wavelengths of 202 to 205 nm or 280 nm, i.e. at the maximum values. The other compounds present in sulfite cooking liquors, however, interfere with the UV-measurement.

Table I shows the interfering components and the maximum percentages of error caused by them at ordinary measurement wavelengths.

TABLE I

Components Interfering With UV-measurements of Sulfite Cooking Liquors and Estimated Maximum Percentages of Error at Different Wavelengths

| Component of spent liquor | Error in residual lignin content, percent of quantity of pulp | | |
|---|---|---|---|
| | 202 nm | 205 nm | 280 nm |
| Organic components | | | |
| Reducing sugars (as mannose) | 0,01 | <0,01 | 0,01 |
| Aldonic acids | 0,06–0,11 | 0,06–0,09 | 0 |
| Glucuronic acid | <0,01 | <0,01 | 0 |
| Furfural | 0,06–0,14 | 0,04–0,11 | 2,26–8,45 |
| Acetic acid | 0,02–0,06 | 0,01–0,05 | 0 |
| Formic acid | <0,01 | <0,01 | 0 |
| Methylglyoxal | 0,01 | 0,01 | 0,01 |
| Other substances | <0,01 | <0,01 | 0 |
| Inorganic components | | | |
| Sulfate | <0,001 | <0,001 | 0 |
| Thiosulfate | 0,01–0,37 | 0,01–0,39 | 0 |
| Tetrathionate | <0,01–0,19 | <0,01–0,24 | 0 |
| Total | 0,17–0,80 | 0,12–0,89 | 2,28–8,48 |
| $SO_2$ 5 g/l | 1,07 | 0,66 | 0 |
| 1 g/l | 0,21 | 0,13 | 0 |

As seen in Table I, pure measurement of lignin is obtained at the wavelength of 280 nm after the non-ionizable compounds have been separated. Another advantage of the wavelength of 280 nm is that the absorptivity is lower, which facilitates the requirement of dilution.

A novel feature of the method of the present invention is that a wavelength of 260 nm provides as reliable a measurement as the maximum value, i.e. 280 nm. At 260 nm, an even somewhat lower absorptivity would be obtained, whereas the quantity of feed could be increased and an even better margin of determination of the monosaccharides be reached.

Optical activity, i.e. the ability to rotate the plane of oscillation of polarized light, is characteristic of compounds that possess so-called asymmetric carbon atoms. In sulfite cooking liquors, such compounds are above all monosaccharides and, to a lower extent, organic acids.

Polarimetric determination of monosaccharides is highly usable, because the phenomenon is completely specific. Lignin or the other optically inactive compounds do not affect the measurement result if the transmittance of the cuvette is only sufficient for the equipment.

The measurement by the refractive index, i.e. the RI-measurement, is believed to be based on the measurement of the difference in refractive index between the two different solutions. The refractive-index detector or RI-detector is a general-purpose detector because all compounds change the refractive index of a solution on being dissolved. The refractive index is linearly dependent on the concentration. Refractive index measurements have, however, been disturbed extensively by contamination of the measurement apparatus. Measurement out of the process liquor by means of a differential refractometer after ion exclusion has not been suggested as an observation method by the prior art.

The method of the present invention allows determination of the concentrations of both lignin and monosaccharides by means of a RI-detector. A deficiency in this measurement technique is that all compounds are eluted at the same time as these compounds to be studied are included in the measurement. However, most of the dry solids in the sulfite spent liquor consist of lignin, and in acid cooks of monosaccharides, so that the concentrations and, in particular, their changes can be established easily.

The essential feature of the method of the present invention is ion-exclusion separation. In order to accomplish this separation, it is required that the filler in the separation column, i.e. the cation-exchange material, be appropriate. The porosity of the cation-exchange material must be sufficient in order to diffuse pentoses and hexoses into the inner volume of the material. An excessively low porosity excludes diffusion sterically. Styrene-divinylbenzene resins have been found useful in this invention. The porosity of the resin is determined by the degree of cross linking, i.e. by the quantity of divinylbenzene. The quantity of divinylbenzene also determines the mechanical strength of the resin, which must be adequate so as to endure a strong flow. Thus, rapid separation requires a resin of particular type. The particle size of the resin is important because a smaller particle size improves the separation, but cause counter-pressure to imcrease. It is important that the counter-pressure be suitable for a simple pump solution. Another factor affecting the ion-exclusion separation is the length of the column, which directly affects the separation time. A suitable length is about 10 to about 40 cm. The flow rate in the column also affects the separation time directly in that the higher flow rate, however, deteriorates the separating ability, i.e. the resolution. An increased temperature increases the rate of diffusion, i.e. improves the separation. On the contrary, the ion-exclusion separation is rather indifferent in respect of changes in the quantity of feed, and the collapsing point of the separation is very high, owing to the nature of group separation. The quantity of feed must, however, be such that the separation is successful and all the detectors operate within an acceptable range. Variation of the size of analytical feeds (<2% of the column volume) does not affect the separation.

The following examples are presented as specific embodiments of the present invention and show some of the unique characteristics of the invention and are not to be considered as constituting a limitation on the present invention.

EXAMPLE 1

In an ion-exclusion column wotj a diameter of 10 mm and length 30 cm, and an ion-exchange material of "DOWEX 50W×4" 100–200 mesh cation-exchange resin in the $Ca^{2+}$ form, which was eluted with pure gas-free water (means that distilled or ion-exchanged water has been evacuated and boiled) at 2.0 ml/min $^{-1}$, at the linear flow rate was 2.55 cm/min$^{-1}$, at a temperature of 50° C., and was fed 50 ul of calcium sulfite cooking liquor from the end of the cooking. The separation time was 10 min, the lignin could be determined in 6 minutes.

In the ultraviolet-spectrophotometric determination of lignin, the detector used was the Knauer UV-filter-photometer with a 0.4 mm flow-through cuvette, and the measurement was carried out at a wavelength of 280 nm. In the polarimetric determination of monosaccharides, a Perkin-Elmer Polarimeter 241 was utilized and a 10 cm flow-through cuvette was used, and the measurement was carried out at a wavelength of 365 nm. In the refractometric determination, both of lignin and of monosaccharides, the Knauer Differential Refractometer was used.

The result curves of the measurements are shown in FIG. 2.

EXAMPLE 2

The procedure was the same as described in Example 1, except that the solution that was analyzed was magnesium-sulfite cooking liquor and the ion-exchange material was "DOWEX 50W×4" 100–200 mesh cation-exchange resin in the $Mg^{2+}$ form. The result curves of the measurements are shown in FIG. 3.

EXAMPLE 3

The procedure was the same as described in Example 1, except that the solution that was analyzed consisted of cooking liquors from a multi-step sodium-sulfite cook:
(A) from the end of the soda step,
(B) from the end of the acid step,
and the ion-exchange material was cation-exchange resin "DOWEX 50W×4" 100–200 mesh in the $Na^+$ form. The result curves of the measurements are shown in FIG. 4.

EXAMPLE 4

The procedure was the same as described in Example 3, except that the solution that was analyzed was sodium-neutral-sulfite-anthraquinone cooking liquor. The result curves of the measurements are shown in FIG. 5.

EXAMPLE 5

The procedure was the same as described in Example 1, except that the quantity of feed was 73 ul, the rate of elution 6.9 ml/min$^{-1}$, i.e. 8.8 cm/min$^{-1}$, the partical side of the ion-exchange resin was 200–400 mesh, and the length of the column was 20 cm for a rapid separation. The separation time was 2.5 min, and the lignin was determined in 1.5 minutes. The result curves of the measurements are shown in FIG. 6.

Obviously, other modifications and variations of the present invention are possible in the light of the above teachings. It is, therefore, to be understood that changes may be made in the particular embodiments of this invention which are within the full intended scope of the invention as defined by the appended claims.

What is claimed is:

1. A method for controlling a sulfite cooking process by determining the lignin, monosaccaride and organic acid contents of sulfite cooking liquor comprising:
   (a) passing a quantity of sulfite cooking liquor containing lignin and monosacharides, lignin and organic acid, or lignin, monosaccharides and organic acids from a sulfite cooking process through a body of cation exchange material under ion-exclusion separation conditions effective to provide an effluent containing a substantially ionic portion and a substantially non-ironic portion;
   (b) determining the content of lignin by UV light analysis and refractive index analysis of said ionic portion, determining the context of monosaccharides by polarimetric analysis of said non-ionic portion, and determining the content of organic acids by refractive index analysis of said non-ionic portion; and
   (c) terminating the sulfide cooking process when the lignin, monosaccharide and organic acid contents reach desired values.

2. A method according to claim 1, wherein said cation exchange material is styrene-divinylbenzene resin having a partical size of 100–200 mesh.

3. A method according to claim 1, wherein said cation exchange material is stryene-divinylbenzene resin having a particle size of about 200–400 mesh.

4. A method according to claim 1, wherein said cation exchange material contains 4 to 5% divinylbenzene.

* * * * *